US012565084B2

(12) United States Patent
Ono et al.

(10) Patent No.: US 12,565,084 B2
(45) Date of Patent: Mar. 3, 2026

(54) AIR PURIFIER

(71) Applicant: NICHIA CORPORATION, Anan (JP)

(72) Inventors: Masato Ono, Sagamihara (JP);
Masayoshi Katsuno, Yokohama (JP)

(73) Assignee: NICHIA CORPORATION, Anan (JP)

( * ) Notice: Subject to any disclaimer, the term of this patent is extended or adjusted under 35 U.S.C. 154(b) by 435 days.

(21) Appl. No.: 18/193,567

(22) Filed: Mar. 30, 2023

(65) Prior Publication Data

US 2023/0311621 A1 Oct. 5, 2023

(30) Foreign Application Priority Data

Mar. 31, 2022 (JP) ................................. 2022-059380

(51) Int. Cl.
*A61L 9/20* (2006.01)
*B60H 3/00* (2006.01)

(52) U.S. Cl.
CPC ............ B60H 3/0078 (2013.01); *A61L 9/205* (2013.01); *A61L 2209/12* (2013.01); *A61L 2209/16* (2013.01)

(58) Field of Classification Search
CPC ....... B60H 3/0071; B60H 3/0078; A61L 9/20; A61L 9/205; A61L 2209/12; A61L 2209/16
See application file for complete search history.

(56) References Cited

U.S. PATENT DOCUMENTS

| | | | |
|---|---|---|---|
| 2015/0098235 A1 | 4/2015 | Singh et al. | |
| 2015/0276163 A1 | 10/2015 | Singh et al. | |
| 2016/0051719 A1 | 2/2016 | Watanabe et al. | |
| 2017/0059973 A1 | 3/2017 | Yamaguchi | |

FOREIGN PATENT DOCUMENTS

| | | | | | |
|---|---|---|---|---|---|
| CN | 107807722 A | * | 3/2018 | ............... | A61L 9/20 |
| JP | 2001-324195 | | 11/2001 | | |
| JP | 2010-102997 | | 5/2010 | | |
| JP | 2010-103018 | | 5/2010 | | |
| JP | 2015-076275 | | 4/2015 | | |
| JP | 2015-187939 | | 10/2015 | | |
| JP | 2016-048683 | | 4/2016 | | |

(Continued)

OTHER PUBLICATIONS

Machine Translation of CN-107807722-A (Year: 2018).*

*Primary Examiner* — Timothy C Cleveland
(74) *Attorney, Agent, or Firm* — MORI & WARD, LLP

(57) ABSTRACT

An air purifier includes a substantially L-shaped support member including a bottom portion and a lateral portion, a substrate disposed on the bottom portion, a light source that is disposed on the substrate and can emit ultraviolet light, a heat sink disposed on the lateral portion and including heat dissipation fins, a substantially L-shaped heat pipe at least partially housed in a recess formed in the support member, and a cover covering at least a part of the heat sink. The bottom portion includes a first surface and a second surface opposite to the first surface. The substrate is disposed on the first surface. The lateral portion includes a third surface joining to the first surface and a fourth surface located opposite to the third surface, and the heat sink is disposed on the third surface. The recess is formed on the second surface and the fourth surface.

18 Claims, 10 Drawing Sheets

(56)            References Cited

FOREIGN PATENT DOCUMENTS

| | | |
|---|---|---|
| JP | 2016-225064 | 12/2016 |
| JP | 2017-045002 | 3/2017 |
| JP | 2017-135083 | 8/2017 |
| JP | 2017-159657 | 9/2017 |
| JP | 2018-084520 | 5/2018 |
| JP | 2018-113229 | 7/2018 |
| JP | 3224213 U | 12/2019 |

* cited by examiner

AIR PURIFIER

CROSS-REFERENCE TO RELATED APPLICATION

This application is based upon and claims priority to Japanese Patent Applications No. 2022-059,380, filed on Mar. 31, 2022, the entire content of which is incorporated herein by reference.

BACKGROUND

The present invention relates to an air purifier.

In Japanese Patent Publication No. 2016-48683, an air purifier including a UV light source and plate-like fins is disclosed. A flow path through which a forced air flow passes is formed between the plate-like fins, and the heat transferred to the plate-like fins is dissipated.

In the apparatus described in Patent Literature 1, there is still room for improvement in terms of the heat transfer from the light source to the plate-like fins, i.e., from the light source to the heat sink.

SUMMARY

An air purifier disclosed in an embodiment includes a substantially L-shaped support member including a bottom portion and a lateral portion, a substrate disposed on the bottom portion, a light source that is disposed on the substrate and can emit ultraviolet light, a heat sink disposed on the lateral portion and including heat dissipation fins, a substantially L-shaped heat pipe at least partially housed in a recess formed in the support member, and a cover covering at least a part of the heat sink. The bottom portion of the support member includes a first surface and a second surface located opposite to the first surface, and the substrate is disposed on the first surface. The lateral portion of the support member includes a third surface joining to the first surface and a fourth surface located opposite to the third surface, and the heat sink is disposed on the third surface. The recess is formed on the second surface and the fourth surface.

In at least one embodiment described herein, an air purifier with enhanced heat transfer from a light source to a heat sink can be provided.

DESCRIPTION

Figure 1:
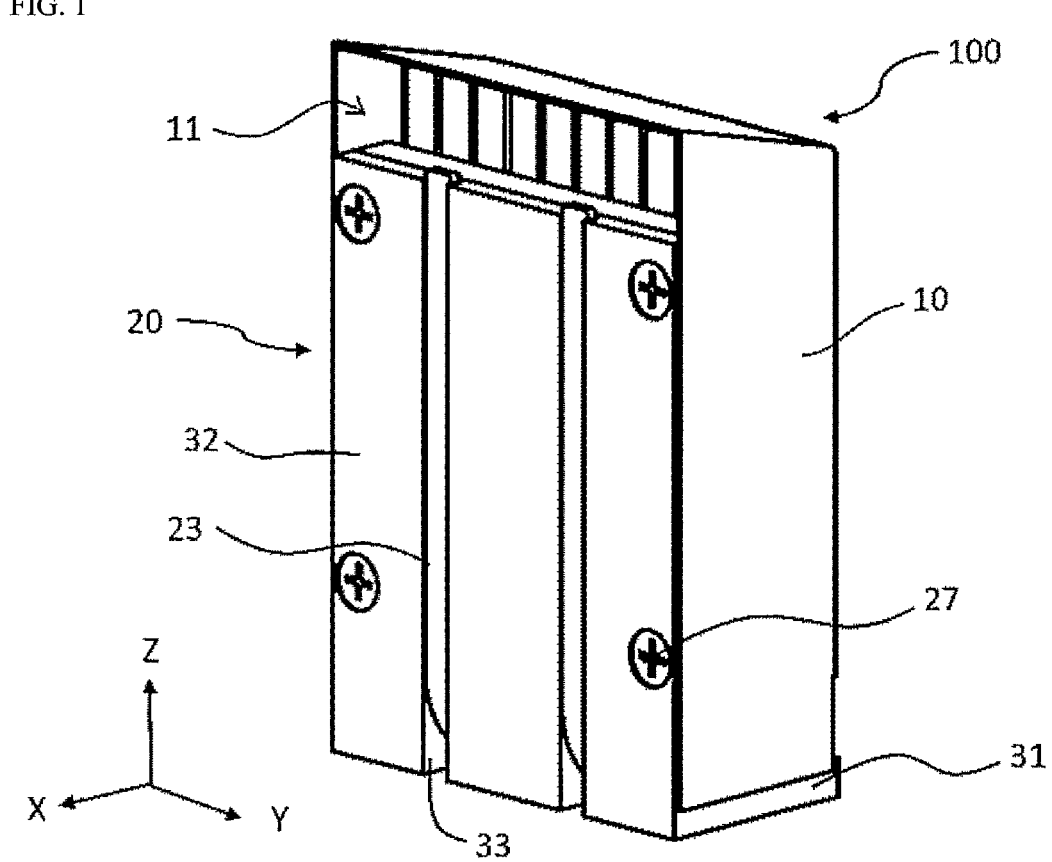
FIG. 1 is a perspective view of an air purifier according to an embodiment.

An air purifier 100 representing one example of an embodiment of the present invention will be described below with reference to FIGS. 1 to 5. The drawings referred to in the following description are diagrams that schematically illustrate the present embodiment, and thus scales and intervals of members, positional relationships, and the like are exaggerated, or some of the members may not be illustrated in the drawings. Furthermore, in the following description, members having the same terms and reference characters, in principle, represent the same members or homogeneous members, and a detailed description of such members will be omitted as appropriate.

For clarity of explanation, the arrangement and structure of respective portions will be described using the XYZ orthogonal coordinate system in the following description. The X, Y, and Z-axes are orthogonal to each other. In the drawings, for directions along the X-axis, the arrowed direction is referred to as a "+X direction", and the opposite direction is referred to as a "−X direction". In addition, for the directions along the Y-axis, the arrowed direction is referred to as a "+Y direction", and the opposite direction is referred to as a "−Y direction". In addition, for the directions along the Z-axis, the arrowed direction is referred to as a "+Z direction", and the opposite direction is referred to as a "−Z direction". The +Z direction is the upward direction and the −Z direction is the downward direction, but these directions have no relation to the direction of gravity.

A view in the +Z direction is referred to as a "top view", a view in the +X direction is referred to as a "front view", and a view in the +Y direction is referred to as a "lateral view". Also, in this description or the scope of the claims, expressions such as upper and lower, left and right, top and bottom, front and back, near and far, and the like are used merely to describe a relative relationship of positions, orientations, directions, and the like, and the expressions may not match an actual relationship at a time of use.

Figure 2:
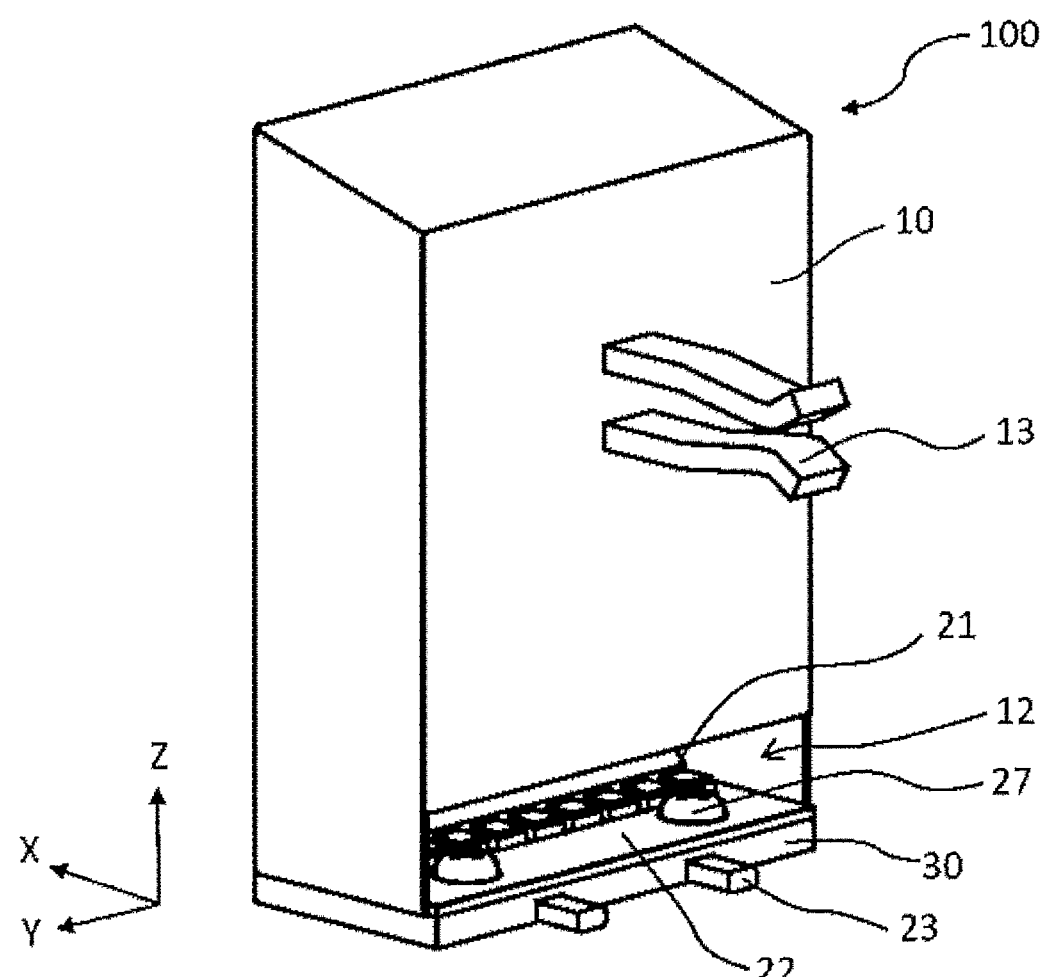
FIG. 2 is a perspective view of a back of the air purifier corresponding to FIG. 1.

An example of an air purifier according to the present embodiment will be described below. The air purifier will be described as an air purifier that is attached to the outlet of an air conditioner of a vehicle and sterilizes the air inside the vehicle. FIG. 1 is a perspective view of the air purifier 100 according to an embodiment, and FIG. 2 is a perspective view of the back surface corresponding to FIG. 1. As illustrated in FIGS. 1 and 2, the air purifier 100 includes a light source unit 20 and a cover 10.

The air purifier 100 irradiates the gas passing through the inside of the air purifier with light emitted from the light source unit 20.

First, each of the components will be described.

Cover

The cover 10 is formed in a box-like shape with a first opening portion 11 formed on the front surface and a second opening portion 12 formed on the back surface. The material of the cover 10 is preferably a material that has light resistance, and Al, SUS, Cu, or the like can be used for the material of the cover 10, for example. From the perspective of UV resistance and high reflectivity with respect to ultraviolet light, Al is preferable.

The cover 10 includes an attachment portion 13 on the back surface (opposite to the front view) of the air purifier 100 that extends in the −X direction. The attachment portion 13 can be an attachment portion for attaching the air purifier to a member such as a louver of the air conditioner of the vehicle, for example.

First Opening Portion

As illustrated in FIG. 1, the air purifier 100 includes the first opening portion 11 on the front. The first opening portion 11 can be said to be a gap formed when the cover 10 and the light source unit 20 are joined. The first opening portion 11 is provided on the upper portion of the air purifier 100 and opens in the YZ plane.

Second Opening Portion

As illustrated in FIG. 2, the air purifier 100 includes the second opening portion 12 on the back. The second opening portion 12 can be said to be a gap formed when the cover 10 and the light source unit 20 are joined. The second opening portion 12 is provided on the lower portion of the air purifier 100 and opens in the YZ plane.

Light Source Unit

Figure 3:
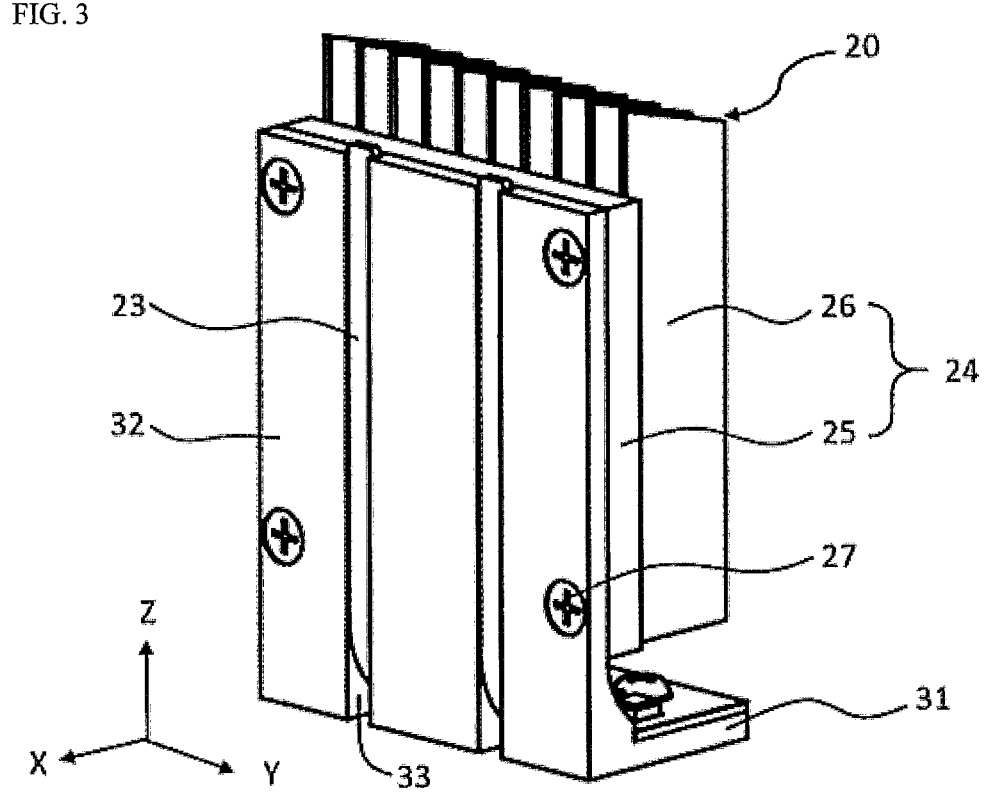
FIG. 3 is a perspective view of a light source unit included in the air purifier according to the embodiment.
Figure 4:
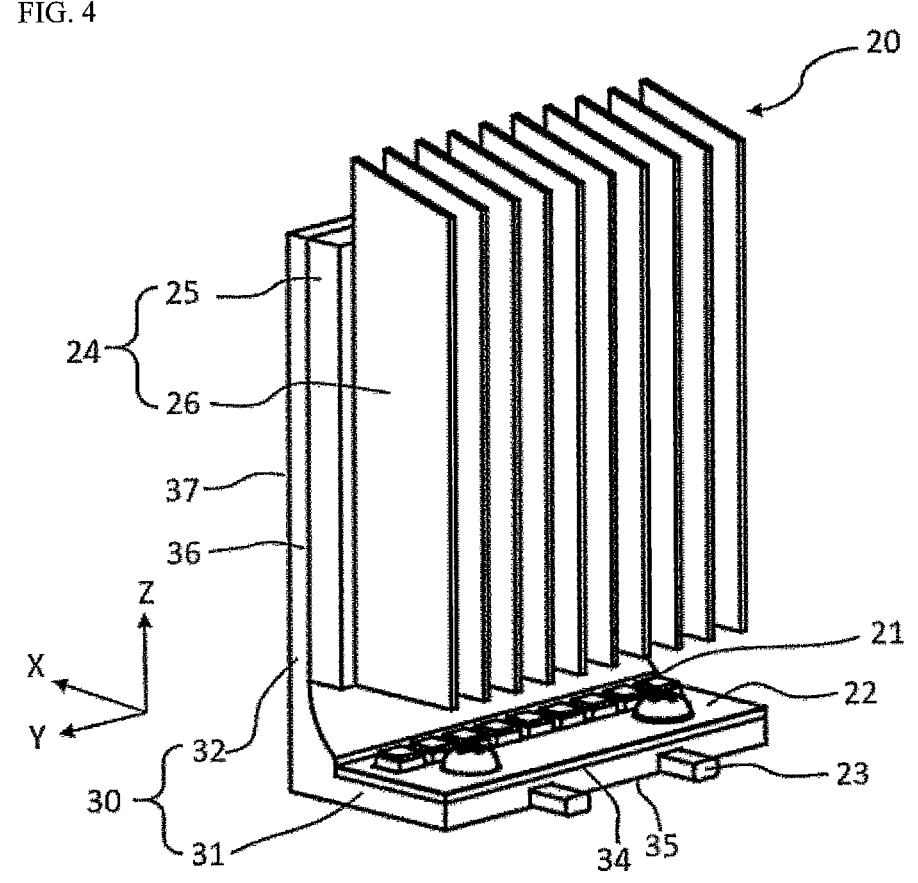
FIG. 4 is a perspective view of a back of the light source unit corresponding to FIG. 3.

FIG. 3 is a perspective view of the light source unit 20, and FIG. 4 is a perspective view of the back of the light source unit 20 corresponding to FIG. 3. As illustrated in FIGS. 3 and 4, the light source unit 20 includes light sources 21, a substrate 22, heat pipes 23, a heat sink 24, and a support member 30.

Light Source

Each of the light sources 21 can emit ultraviolet light. A peak emission wavelength of the ultraviolet light emitted by the light source 21 is, for example, in a range from 250 nm to 410 nm, and more preferably in a range from 250 nm to 290 nm. The peak emission wavelength of the ultraviolet light emitted by the light source 21 is not limited to this wavelength range. The light source 21 includes a light-emitting element. As the light-emitting element, a light emitting diode (LED) or a laser diode (LD) can be used, for example.

Examples of the light-emitting element include a light-emitting element including an active layer formed of a GaN-based material. Examples of the GaN-based material include GaN, InGaN, and AlGaN.

Substrate

The substrate 22 is, for example, a wiring substrate including an insulating layer and wires electrically connected to the light source 21. The substrate 22 is substantially flat plate-like shape in the present embodiment. The substrate 22 includes an upper surface and a lower surface, and the upper surface and the lower surface are substantially flat surfaces. However, the shape of the substrate is not limited to the above. For example, the substrate can include uneven surfaces. Two through-holes are provided in the substrate 22 for receiving screws. The through-holes penetrate the substrate 22 in the Z direction.

The substrate 22 is, for example, a metal substrate provided with an insulating layer on the surface of a metal plate. Examples of the metal material include Al, Cu. From the perspective of weight reduction and heat dissipation, Al is preferred. The thermal conductivity of the metal plate of the substrate 22 is, for example, in a range from 150 W/mK to 200 W/mK, and the thermal conductivity of the insulating layer of the substrate 22 is, for example, in a range from 1 W/mK to 10 W/mK.

Heat Pipe

Each of the heat pipes 23 is a member that functions as a heat conductor. The heat pipe 23 transports heat by phase change such as evaporation and condensation of liquid enclosed within the container. In the present embodiment, a cylindrical heat pipe is used, but a prism-shaped heat pipe 23 can be used.

For the material of the container portion of the heat pipe 23, for example, Cu, Al, SUS, or the like can be used, and Cu is preferable from the perspective of thermal conductivity and bend forming. The surface of the container can be subjected to plating treatment, and as the plating material, Ni, Sn, or the like can be used. The liquid enclosed in the heat pipe 23 can be, for example, water, chlorofluorocarbon, methanol, and the like, and water is preferred from the perspective of reducing the vapor pressure in the operating temperature range (for example, from 10° C. to 100° C.). The heat pipe 23 is vacuum sealed to suppress degradation.

The thermal conductivity of the heat pipe 23 is, for example, in a range from 2000 W/mK to 100000 W/mK.

When the heat pipe 23 has a cylindrical shape, the diameter of the pipe is, for example, in a range from 3 mm to 10 mm. When the heat pipe 23 has a prism shape, the length of one side of the rectangular cross-section of the pipe in the shorter direction is, for example, in a range from 3 mm to 10 mm.

Because the heat pipe 23 is disposed along the support member 30 described below, the heat pipe 23 is substantially L-shaped in the XZ plane. The shape of the heat pipe 23 is not limited to this and can be changed in accordance with the shape of the support member 30. That is, the bending angle and the bending position of the heat pipe 23 can be changed as appropriate.

Heat Sink

The heat sink 24 is a member that functions as a heat conductor in a similar manner to the heat pipe 23. The heat sink 24 includes a base plate 25 and a plurality of heat dissipation fins 26. The base plate 25 and the heat dissipation fins 26 are formed of the same material and are formed of a metal material having good thermal conductivity.

The base plate 25 is a flat plate disposed parallel to the YZ plane, and the plurality of heat dissipation fins 26 disposed parallel to the XZ plane are joined to the surface of the base plate 25 on the −X direction. Four through-holes are provided in the base plate 25 for receiving screws. The through-holes penetrate the base plate 25 in the X direction. The heat dissipation fins 26 are flat plates that are thinner than the base plate 25 and arranged at intervals in the Y direction. A groove-like flow path extending in the Z direction is formed by being surrounded by three surfaces, i.e., the surfaces of adjacent heat dissipation fins 26 and the surface of the base plate 25. The distance between adjacent heat dissipation fins 26 is, for example, in a range from 4 mm to 10 mm.

The material of the heat sink 24 can be, for example, Al, Cu, or the like, and from the perspective of heat dissipation and weight reduction, Al having high heat dissipation and a low specific gravity is preferable. Furthermore, it is preferable that the surface of the heat sink 24 can suppress absorption of light irradiated from the light source 21 and reflect the light. The surface of the heat sink 24 preferably has, for example, a reflectivity of 90% or greater with respect to the peak wavelength of the light irradiated from the light source 21. For example, Al having a high reflectivity with respect to ultraviolet light is preferable for the material on the surface of the heat sink 24. Furthermore, the thickness of each of the heat dissipation fins 26 is preferably thin so that light can easily enter the flow paths and is preferably in a range from 0.5 mm to 2 mm, for example.

The thermal resistance of the heat sink 24 is, for example, in a range from 0.01° C./W to 10° C./W.

Support Member

The support member 30 is a substantially L-shaped member including a bottom portion 31 and a lateral portion 32. The material of the support member 30 is, for example, Al, Cu, or the like. From the perspective of heat dissipation and weight reduction, Al having high heat dissipation and a low specific gravity is preferable for the material of the support member 30.

The bottom portion 31 and the lateral portion 32 of the support member 30 can be integrally formed with the same member or can be formed by joining separate members.

The bottom portion 31 of the support member 30 includes a first surface 34 and a second surface 35 located opposite to the first surface 34. Also, the lateral portion 32 of the support member 30 includes a third surface 36 that joins to the first surface 34 and a fourth surface 37 located opposite to the third surface 36.

Each of the bottom portion 31 and the lateral portion 32 has a substantially flat plate-like shape. The first surface 34 and the second surface 35 are disposed in the XY plane and are parallel to one another. The third surface 36 and the fourth surface 37 are disposed in the YZ plane and are parallel to one another. The thickness (Z direction) of the bottom portion 31 is, for example, in a range from 2 mm to 5 mm. The thickness (X direction) of the lateral portion 32 is, for example, in a range from 2 mm to 5 mm.

In the present embodiment, the support member 30 is substantially L-shaped with an approximate 90° angle formed by the bottom portion 31 and the lateral portion 32 of the support member 30. However, no such limitation is intended. For example, the angle formed by the bottom portion 31 and the lateral portion 32 can be in a range from 60° to 120°.

Groove-like recesses 33 are formed on the second surface 35 and the fourth surface 37 of the support member 30. The recess 33 formed on the second surface 35 and the recess 33 formed on the fourth surface 37 are connected, and the L-shaped heat pipe 23 described above can be housed in the recesses 33. The depth of the recess is, for example, in a range from 50% to 80% of the thickness of the bottom portion 31 and the lateral portion 32.

Two through-holes are provided in the bottom portion 31 of the support member 30 for receiving screws. The through-holes penetrate the bottom portion 31 in the Z direction. Also, four through-holes are provided in the lateral portion 32 for receiving screws. The through-holes penetrate the lateral portion 32 in the X direction.

Next, the air purifier 100 will be described by using FIGS. 1 to 4.

Air Purifier

The air purifier 100 includes the light source unit 20 and the cover 10, and the cover 10 covers the back surface of the light source unit 20. At least a part of the heat sink 24 is covered by the cover 10. The front surface of the light source unit 20 is exposed to the outside of the cover 10. The cover 10 and the light source unit 20 are joined by fitting.

The substrate 22 is disposed on the first surface 34, which is on the bottom portion 31 of the support member 30 of the light source unit 20. The support member 30 and the substrate 22 are screwed together at two positions by using screw holes formed in the bottom portion 31 of the support member 30 and the substrate 22.

The heat sink 24 is disposed on the third surface 36 of the lateral portion 32 of the support member 30. The support member 30 and the heat sink 24 are screwed together at four positions by using screw holes formed in the lateral portion 32 of the support member 30 and the base plate 25 of the heat sink 24.

The plurality of light sources 21 are disposed on the substrate 22 along the Y direction (first direction). The light source 21 is typically an LED, and the external electrode of the LED and the wire of the substrate 22 are electrically and mechanically joined by an electrically conductive joint member such as a solder. The number of light sources 21 is in a range from 6 to 12, for example, but no such limitation is intended. As illustrated in FIGS. 2 and 4, nine LEDs are disposed in a row in the air purifier 100. Additionally, the arrangement of the plurality of light sources 21 is not limited to a single row, and the plurality of light sources 21 can be arranged in 2 rows or can be arranged in a zigzag pattern extending in the Y direction.

The flow paths formed by the heat sink 24 and extending in the Z direction (second direction) intersect the Y direction. In other words, the direction in which the light sources 21 are arranged and the direction in which the flow paths formed by the heat dissipation fins 26 extend intersect one another.

Each of the plurality of light sources 21 is disposed on an extended line of the corresponding one of the flow paths formed by the heat sink 24. The expression "disposed on the extended line of the corresponding one of the flow paths" means that the center of each of the light sources 21 in the Y direction is substantially aligned with the center of the corresponding one of the flow paths in the Y direction. In other words, the light source 21 is disposed, in the Y direction, between adjacent heat dissipation fins 26. The advantage of the light source 21 being disposed on the extended line of the flow path formed by the heat sink 24 is described below.

The flow path is formed as a groove portion formed by being surrounded by the base plate 25 and adjacent heat dissipation fins 26, but the flow path can be surrounded by four surfaces by disposing the surface of the cover 10 so as to be orthogonal to the plate surface of the flat plate-like heat dissipation fins 26.

The heat pipe 23 is housed in the recess 33 formed in the support member 30. In the present embodiment, the entire heat pipe 23 is housed inside the recess so as not to protrude from the second surface 35 of the bottom portion 31 and the fourth surface 37 of the lateral portion 32. However, a part of the heat pipe 23 can protrude from the second surface 35 and/or the fourth surface 37.

Figure 5:
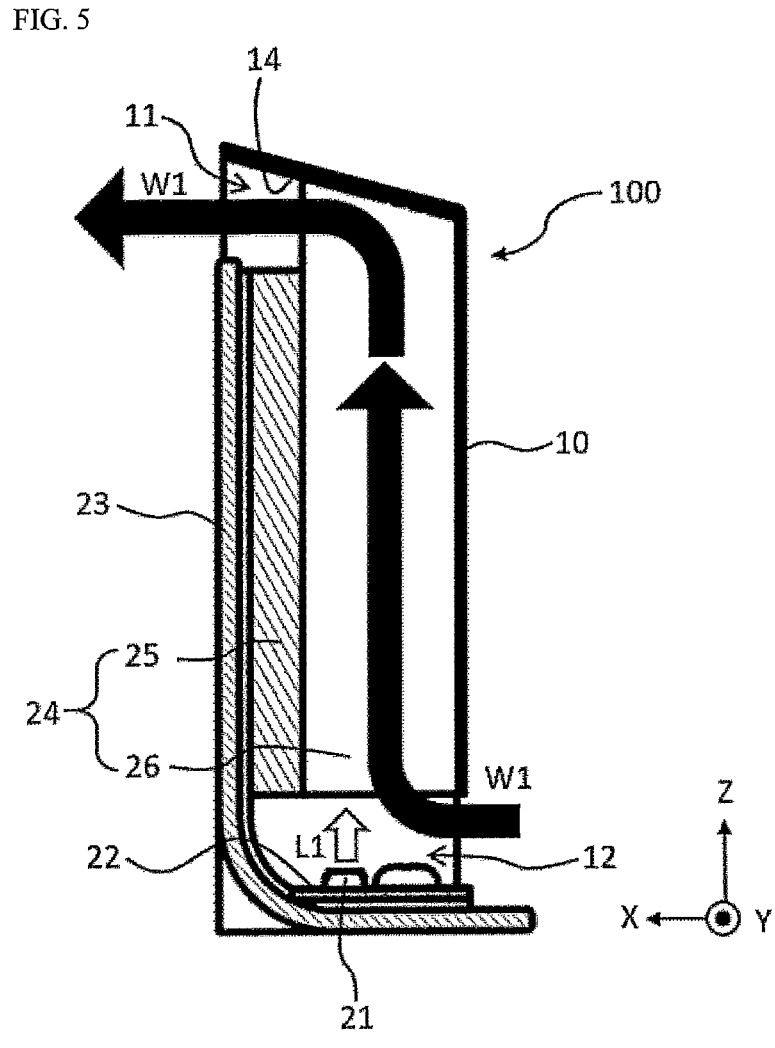
FIG. 5 is a cross-sectional view of FIG. 2 taken along a plane parallel to an XZ plane.

As illustrated in FIGS. 3 to 5, the upper end portion (the upper end in the Z direction) of the heat pipe 23 is located at substantially the same position as the upper portion (the upper end in the Z direction) of the base plate 25. On the other hand, the lower end portion (the end portion in the X direction) of the heat pipe 23 protrudes from the end surface of the substrate 22 in the −X direction.

FIG. 5 is a cross-sectional view of the air purifier 100 of FIG. 2 taken along a plane parallel to the XZ plane. As described above, the heat pipe 23 is housed in a recess 33 formed in the bottom portion 31 and the lateral portion 32 of the support member 30. With this configuration, heat generated when the light source 21 irradiates light can be efficiently dissipated to the heat sink 24. Specifically, the heat from the light source 21 is transferred from the substrate 22 to the bottom portion 31 of the support member 30 and transferred along the heat pipe 23 to the heat sink 24 via the lateral portion 32 of the support member 30. This configuration improves heat transfer from the light source 21 to the heat sink 24.

In the air purifier 100, the light emitted from the light source 21 is irradiated along the Z direction toward the heat sink 24. In FIG. 5, the emission direction L1 of the light is illustrated as an arrow. The flow path is also a portion through which light from the light source 21 passes. Thus, the heat sink 24 has not only the function of dissipating the heat from the light source 21, but also functions as a reflector that reflects the light from the light sources 21. It is preferable that the four surfaces surrounding the flow path can suppress absorption of the light irradiated from the light source 21 and reflect the light. For example, a reflectivity of 90% or greater is preferable with respect to the peak wavelength of the light irradiated from the light source 21.

By surrounding the flow path by using four surfaces with a high reflectivity, light can be guided to the upper portion of the heat dissipation fins 26.

The air purifier 100 is used, for example, by attaching the attachment portion 13 to the outlet of an air conditioner of a vehicle. The second opening portion 12 is provided on the back of the air purifier 100 provided with the attachment portion 13. In FIG. 5, a gas flow W1 is illustrated by arrows. The gas that enters from the second opening portion 12 passes through the flow paths formed by the heat dissipation fins 26 of the heat sink 24 and is discharged from the first opening portion 11. That is, the first opening portion 11 can be used as an outlet and the second opening portion 12 can be used as an inlet.

By irradiating the gas (air) flowing through the flow paths with the ultraviolet light emitted from the light sources 21, bacteria floating in the gas is irradiated with light and can be sterilized. The air taken into the air purifier 100 from the second opening portion 12 is sterilized and discharged from the first opening portion 11.

The heat sink 24 is cooled by gas flowing through the flow paths. In the present embodiment, the heat sink 24 irradiated with light functions as both a sterilization space with a surface that can reflect light and as a heat dissipation member that can air-cool the heat from the light source 21.

Heat sinks are typically disposed near the light source to dissipate the heat from the light source. However, disposing the heat sink near the light source increases the size of the apparatus. In the present embodiment, as described above, the heat sink 24 functions as both a heat dissipation member and a light-guiding member. Thus, an air purifier with a compact size and high light irradiation efficiency can be achieved.

As illustrated in FIG. 5, a wavelength conversion member 14 can be disposed on the inner upper surface of the cover 10 at a position visible from the outside through the first opening portion 11. The wavelength conversion member 14 absorbs the light from the light source 21 and emits light with a different wavelength from that of the light from the light source 21. Because the ultraviolet light is not visible to the human eye, it is difficult to visually determine whether the air purifier 100 is operating. By providing the wavelength conversion member 14 that absorbs ultraviolet light and emits light, it is possible to visually recognize that the air purifier is operating by the emission of light by the wavelength conversion member 14 when the air purifier is operating.

The wavelength conversion member 14 is made of a resin containing phosphor particles, for example. Examples of phosphor particles include blue phosphor particles, such as $BaMgAl_{10}O_{17}$:Eu, $(Sr,Ca,Ba)_{10}(PO_4)_6Cl_2$:Eu, and the like; green phosphor particles, such as $LaPO_4$:Ce, Tb, $ZnSiO_2$: Mn, and the like; and red phosphor particles, such as $Y_2O_3$:Eu, $Y(PV)O_4$:Eu, $Y_2O_2S$:Eu, $3.5MgO\cdot0.5MgF_2\cdot GeO_2$:Mn, and the like.

A photocatalyst can be disposed at a location inside the cover 10 where light from the light source 21 is irradiated. By disposing the photocatalyst, the deodorizing function of the air purifier can be improved. The photocatalyst can be disposed on the surface of the heat dissipation fins 26, but heat is generated by the photocatalyst absorbing ultraviolet light. Furthermore, because the light reflectivity also decreases, more heat is generated. Because the heat dissipation decreases in this manner, the photocatalyst is preferably not disposed on the heat dissipation fins 26.

In addition to the light source 21, a temperature sensor such as a thermistor can be disposed on the substrate 22. The temperature sensor detects the temperature near the light source 21. If the volume of air hitting the light source 21 decreases, the light source 21 will not be air-cooled, and thus the substrate temperature near the light source 21 increases. By providing a circuit for stopping the power supply to the light source 21 when the temperature reaches a certain temperature or greater, a fail-safe function can be provided that can turn off the light source 21 when there is no air being blown.

Figure 8A:
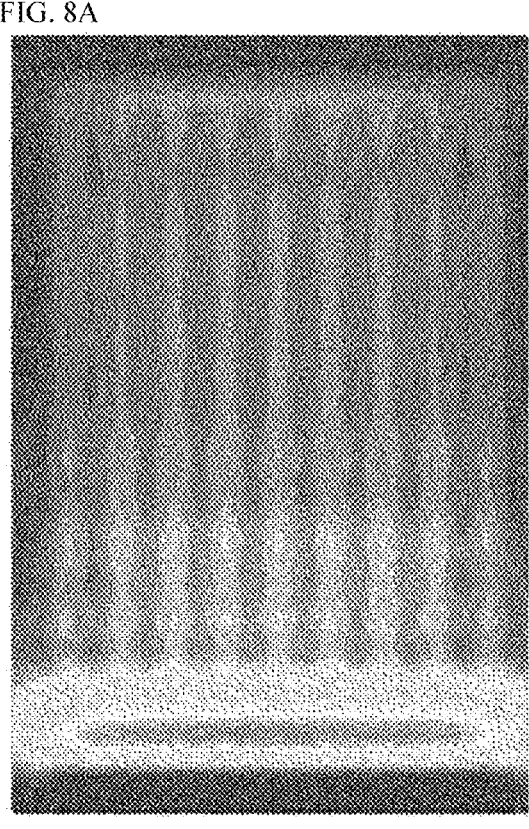
FIGS. 8A to 8C are schematic diagrams illustrating irradiation distribution of light from a light source of the air purifier according to the embodiment.
Figure 8B:
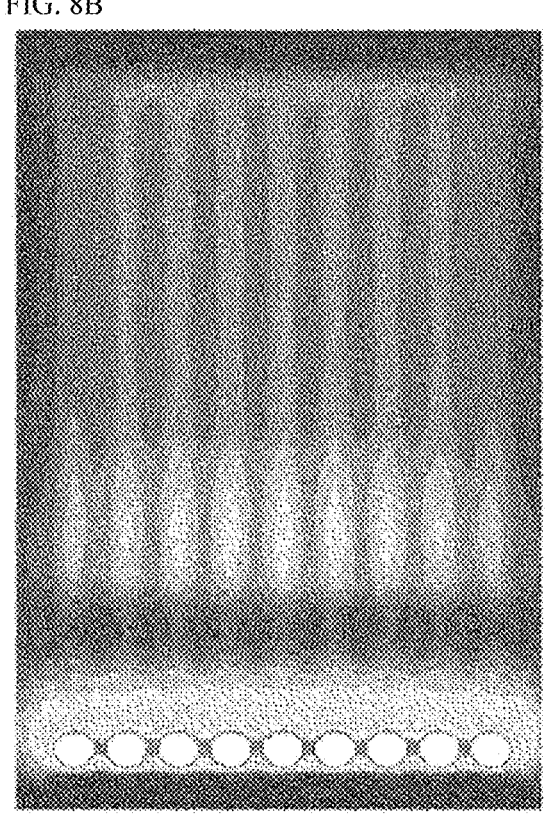
Figure 8C:
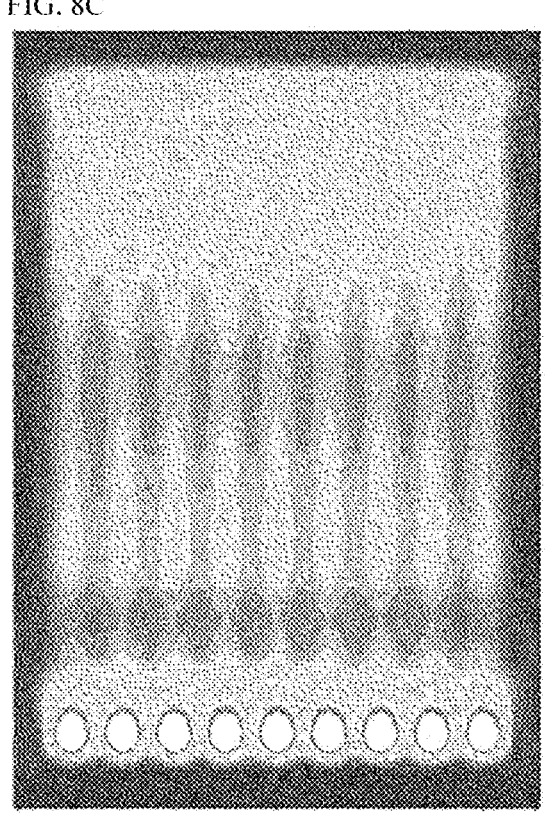

Next, the advantage of the light source 21 being disposed on the extended line of the flow path formed by the heat sink 24 will be described. FIGS. 8A to 8C are YZ plane views illustrating simulation results of irradiation distribution of the light from the light sources 21 in the state illustrated in FIG. 4. Whiter regions have larger amounts of irradiation, and blacker regions have lower amount of irradiation. The bottom of the paper is the region where the light sources 21 are disposed.

In FIG. 8A, the center of each of the light sources 21 was disposed on the extended line of the corresponding one of the heat dissipation fins 26 in the YZ plane. In FIGS. 8B and 8C, the center of each of the light sources 21 was disposed in the center of the corresponding one of the flow paths in the YZ plane. In FIGS. 8A and 8B, 50% power angle (2θ½) of the light sources 21 was 110°, whereas in FIG. 8C, 50% power angle (2θ½) of the light sources 21 was 60°.

As illustrated in FIG. 8A, when the center of each of the light sources 21 was disposed on the extended line of the corresponding one of the heat dissipation fins 26, the light irradiation amount toward the upper portion of the heat sink 24 was insufficient as compared to the arrangement illustrated in FIGS. 8B and 8C. In contrast, as can be seen in the arrangement of FIG. 8B in which the center of each of the light sources 21 was disposed on the center of the corresponding one of the flow paths, the upper portion of the heat sink 24 was irradiated with light as compared to the arrangement illustrated in FIG. 8A. Furthermore, it can be seen that, as illustrated in FIG. 8C, by narrowing the light distribution of each of the light sources 21, the light was uniformly irradiated up to the upper portion of the heat sink 24.

If the integrated irradiation amount of light irradiated to the air discharged from the outlet of the air purifier with the arrangement illustrated in FIG. 8A was defined as 100%, the integrated irradiation amount of the arrangement illustrated in FIG. 8B was 112%, and the integrated irradiation amount of the arrangement illustrated in FIG. 8C was 140%. This result shows that the center of each of the light sources 21 is preferably disposed at the center of the corresponding one of the flow paths and that light is preferably irradiated between the heat dissipation fins 26 with the light sources 21 each having a narrow light distribution angle.

Figure 6:
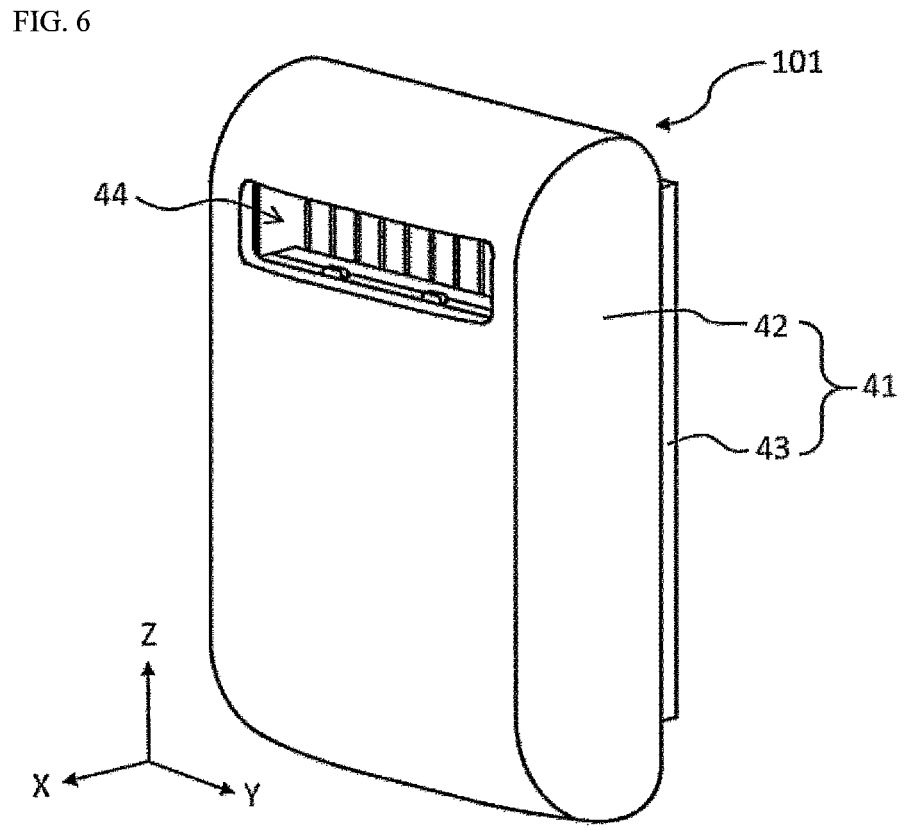
FIG. 6 is a perspective view of another example of the air purifier according to the embodiment.
Figure 7:
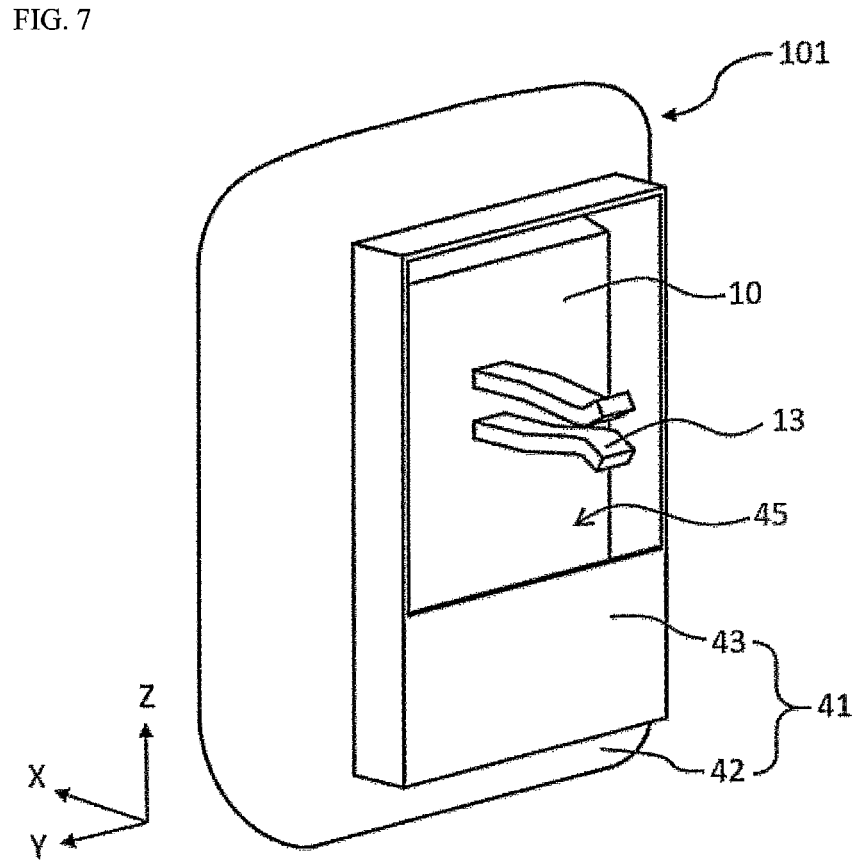
FIG. 7 is a perspective view of a back of the air purifier corresponding to FIG. 6.

FIGS. 6 and 7 illustrate examples in which the air purifier 100 illustrated in FIGS. 1 and 2 is housed in a housing 41.

Housing

The housing 41 is a housing including a main body 42 having a vertical rectangular parallelepiped shape and a protrusion 43 protruding in the −X direction from the main body 42. A third opening portion 44 is provided in the upper portion on the front of the main body 42 of the housing 41, and a fourth opening portion 45 is provided from a central portion to the upper portion on the back of the protrusion 43. The protrusion 43 protrudes in a manner that allows air to efficiently enter the second opening portion 12 and is hollow.

The opening shape of the third opening portion 44 is a rectangle that is longer in the Y direction than in the Z direction, and the opening shape of the fourth opening portion 45 is a rectangle that is longer in the Z direction than in the Y direction. The third opening portion 44 is formed at a position overlapping the first opening portion 11 and functions as an outlet in a similar manner to the first opening portion 11. The fourth opening portion 45 functions as an inlet in a similar manner to the second opening portion 12, but the fourth opening portion 45 and the second opening portion 12 do not overlap in terms of position and are formed at different positions. With this configuration, the light sources 21 are not exposed to the outside. Also, by the opening area of the fourth opening portion 45 being made larger than the opening area of the second opening portion 12, the amount of air taken in can be increased. The second opening portion 12 is covered by the protrusion 43 of the housing 41.

As illustrated in FIG. 7, the attachment portion 13 protrudes from the fourth opening portion 45. A part of the cover 10 of the air purifier 100 is exposed via the fourth opening portion 45. The gas taken in from the fourth opening portion 45 flows in the −Z direction and is taken in from the second opening portion 12.

The main body 42 of the housing 41 is not directly irradiated with ultraviolet light. Thus, the material that can be used for the main body 42 is, for example, a resin such as ABS, PC, PMMA, and the like. The protrusion 43 is preferably made of Al, SUS, or the like due to it being irradiated with ultraviolet light.

Experiment

The following characteristics were measured under the assumption that an air purifier 101 according to an embodiment illustrated in FIGS. 6 and 7 is attached to the air conditioner of a typical vehicle.

Light source used: LED with a peak wavelength of 280 nm

Air purifier external size: 100 mm×75 mm×35 mm

Input Power: 18 W

LED radiant flux: 560 mW

Outlet blowing speed: 1.8 m/s

LED surface temperature: 54.9° C.

Integrated irradiation amount of light irradiated to the air discharged from the outlet of the air purifier: 2.3 mJ/cm2

Volume of air discharged from the outlet of the air purifier: 0.05 m³/min

Typical vehicle interior volume: 3.6 m³

Also, an inactivation experiment for microdroplet-sized novel coronavirus (alpha strain, UK variant) was performed by using an LED with a peak wavelength of 280 nm made in a similar manner to the light source used. As a result, after one-pass test, the infectivity at an integrated irradiation amount of approximately 1 mJ/cm² was confirmed to be $\frac{1}{10}$ or less (virus survival rate of 4.5%).

From these results, it was predicted that, when the air purifier 101 according to the present embodiment is attached to the air conditioner of a typical vehicle, 95% or more of the novel coronavirus can be inactivated in approximately 72 minutes. It was also found that the surface temperature of the LED was suppressed to approximately 55 degrees, and appropriate heat dissipation was achieved.

As described above, the present invention having the technical features disclosed in the description is not necessarily limited to the structure described in the embodiments of the description. For example, the present invention can be applied to an air purifier including components not disclosed in the embodiments.

An air purifier described in an embodiment can be used as an air purifier that is to be attached to the air conditioner of a vehicle. The present invention is not limited thereto and can also be used for air conditioning systems, for sterilization of entire buildings such as nursing homes, hospitals, and other buildings, for sterilization of clean rooms, and the like.

It is to be understood that, although certain embodiments of the present invention have been described, various other embodiments and variants may occur to those skilled in the art that are within the scope and spirit of the invention, and such other embodiments and variants are intended to be covered by the following claims.

REFERENCE SIGNS LIST

100, 101 Air purifier
10 Cover
11 First opening portion
12 Second opening portion
13 Attachment portion
14 Wavelength conversion member
20 Light source unit
21 Light source
22 Substrate
23 Heat pipe
24 Heat sink
25 Base plate
26 Heat dissipation fin
27 Screw
30 Support member
31 Bottom portion
32 Lateral portion
33 Recess
34 First surface
35 Second surface
36 Third surface
37 Fourth surface
41 Housing
42 Main body
43 Protrusion
44 Third opening portion
45 Fourth opening portion

What is claimed is:

1. An air purifier comprising:
a substantially L-shaped support member comprising a bottom portion and a lateral portion such that the lateral portion extends perpendicular to the bottom portion;
a substrate disposed on the bottom portion;
a light source disposed on the substrate and configured to emit ultraviolet light;
a heat sink disposed on the lateral portion and comprising heat dissipation fins;
a substantially L-shaped heat pipe configured to be at least partially housed in a recess formed in the support member; and
a cover covering at least a part of the heat sink, wherein
the bottom portion of the support member comprises a first surface and a second surface located opposite to the first surface, and the substrate is disposed on the first surface,
the lateral portion of the support member comprises a third surface joining to the first surface and a fourth surface located opposite to the third surface, the heat sink being disposed on the third surface, the first surface facing toward the heat sink, and
the recess is formed on the second surface and the fourth surface.

2. The air purifier according to claim 1, wherein
the light source comprises a plurality of the light sources that are disposed along a first direction, and flow paths formed by the heat dissipation fins extends along a second direction intersecting the first direction.

3. The air purifier according to claim 2, wherein each of the plurality of the light sources is disposed on an extended line of a corresponding one of the flow paths.

4. The air purifier according to claim 1, wherein the light source is an LED with a peak emission wavelength in a range from 250 nm to 290 nm.

5. The air purifier according to claim 1, wherein a surface of the heat sink comprises Al.

6. The air purifier according to claim 1, wherein a wavelength conversion member is disposed inside the cover at a position where the wavelength conversion member can be seen from outside.

7. The air purifier according to claim 1, wherein a photocatalyst is disposed inside the cover.

8. The air purifier according to claim 1, wherein a temperature sensor is disposed on the substrate.

9. The air purifier according to claim 1, wherein the air purifier is configured to be attached to an air conditioner of a vehicle.

10. An air purifier comprising:
a support member comprising a bottom portion and a lateral portion;
a substrate disposed on the bottom portion;
a light source disposed on the substrate and configured to emit ultraviolet light;
a heat sink disposed on the lateral portion and comprising heat dissipation fins;
a heat pipe disposed in a recess formed in the support member; and
a cover covering at least a part of the heat sink, wherein
the bottom portion of the support member comprises a first surface and a second surface located opposite to the first surface, and the substrate is disposed on the first surface, the lateral portion of the support member comprises a third surface joining to the first surface and a fourth surface located opposite to the third surface, the heat sink being disposed on the third surface, the first surface facing toward the heat sink, and the recess is formed on the second surface and the fourth surface.

11. The air purifier according to claim 10, wherein the light source comprises a plurality of the light sources that are disposed along a first direction, and flow paths formed by the heat dissipation fins extends along a second direction intersecting the first direction.

12. The air purifier according to claim 11, wherein each of the plurality of the light sources is disposed on an extended line of a corresponding one of the flow paths.

13. The air purifier according to claim 10, wherein the light source is an LED with a peak emission wavelength in a range from 250 nm to 290 nm.

14. The air purifier according to claim 10, wherein a surface of the heat sink comprises Al.

15. The air purifier according to claim 10, wherein a wavelength conversion member is disposed inside the cover at a position where the wavelength conversion member can be seen from outside.

16. The air purifier according to claim 10, wherein a photocatalyst is disposed inside the cover.

17. The air purifier according to claim 10, wherein a temperature sensor is disposed on the substrate.

18. The air purifier according to claim 10, wherein the air purifier is configured to be attached to an air conditioner of a vehicle.

* * * * *